US010478160B1

(12) United States Patent
Mooney et al.

(10) Patent No.: US 10,478,160 B1
(45) Date of Patent: Nov. 19, 2019

(54) TECHNOLOGIES FOR CARTILAGE HARVESTING

(71) Applicants: Christopher M. Mooney, Summit, NJ (US); Riley Joseph Williams, III, New York, NY (US)

(72) Inventors: Christopher M. Mooney, Summit, NJ (US); Riley Joseph Williams, III, New York, NY (US)

( * ) Notice: Subject to any disclaimer, the term of this patent is extended or adjusted under 35 U.S.C. 154(b) by 147 days.

(21) Appl. No.: 15/494,327

(22) Filed: Apr. 21, 2017

Related U.S. Application Data

(60) Provisional application No. 62/325,615, filed on Apr. 21, 2016.

(51) Int. Cl.
*A61B 10/02* (2006.01)
*A61B 17/16* (2006.01)

(52) U.S. Cl.
CPC ........ *A61B 10/025* (2013.01); *A61B 17/1604* (2013.01); *A61B 17/1659* (2013.01); *A61B 2010/0208* (2013.01)

(58) Field of Classification Search
CPC ........................ A61B 10/025; A61B 17/1604
See application file for complete search history.

(56) References Cited

U.S. PATENT DOCUMENTS

| 4,936,313 | A | 6/1990 | Burkhardt et al. |
| 6,264,211 | B1 | 7/2001 | Granado |
| 6,544,260 | B1 * | 4/2003 | Markel .......... A61B 17/320016 606/41 |
| 7,192,431 | B2 | 3/2007 | Hangody et al. |
| 8,622,667 | B1 | 1/2014 | Seay |
| 8,641,764 | B2 | 2/2014 | Gately |
| 9,020,577 | B2 | 4/2015 | Reach, Jr. |
| 9,216,022 | B2 | 12/2015 | Karnes et al. |
| 9,232,953 | B2 | 1/2016 | Bono |

(Continued)

FOREIGN PATENT DOCUMENTS

WO  WO2015112469  7/2015

OTHER PUBLICATIONS

ACT allograft cartilage transplant surgical technique, http://www.mtf.org/documents/PI_-43_Rev_4.pdf, downloaded from the Internet May 18, 2016 (2 pages).

(Continued)

*Primary Examiner* — Olivia C Chang
(74) *Attorney, Agent, or Firm* — Dentons US LLP

(57) ABSTRACT

Various technologies for cartilage harvesting are provided. Some of the technologies include a method including coupling a cutting head onto an actuator; applying a force to the cutting head via the actuator; and cutting a cartilage with the cutting head based on the force. Some of the technologies include a method including coupling an adapter to a rotary tool, wherein the adapter adapts the rotary tool from a rotary power to an impact power; coupling a cutting head to the adapter; applying a force to the cutting head via the adapter; and cutting a cartilage with the cutting head based on the force. Some of the technologies include a device including a cutting head hosting a plug that is able to travel within the cutting head. Some of the technologies may include an extracted chondrocyte including a sidewall inclined from about five degrees to about twenty five degrees.

19 Claims, 15 Drawing Sheets

(56) References Cited

U.S. PATENT DOCUMENTS

| | | |
|---|---|---|
| 9,301,766 B2 | 4/2016 | Berelsman et al. |
| 2007/0131440 A1 | 6/2007 | Hashimoto et al. |
| 2010/0211173 A1 | 8/2010 | Bárdos et al. |
| 2014/0180414 A1* | 6/2014 | Pfeiffer .............. A61B 17/1635 623/16.11 |
| 2014/0236306 A1* | 8/2014 | Karnes ................ A61F 2/30756 623/20.16 |
| 2015/0105696 A1 | 4/2015 | Litke et al. |

OTHER PUBLICATIONS

BioUni Oats Surgical Technique, http://secure.cdn.arthrex.com/pdfs/ 8BvMIV5oukmlqQFS0U7MgQ/8BvMIV5oukmlqQFS0U7MgQ. pdf?Expires=1463565587&Signature=DPr-7pOJGG8O6dX6QF5x nlF5Kt7~tXBU~8imjWVAYU47ZVEKTHdUTjqMQkbpNqLyHM AKC5DtJaZqMVszMRhUgxdqpf217nV2og3FY4CWqFXnFKRZ2 vj749xvlGVmyefMahsoTMG2Jf0Sx4TjdGjKtk2gLteiZZ4ZftaNcW FVX9INzorW1iq8yHx7N8akbf3SiS05MBC71ee2gO7S-f-ZHzdpx ~B7Vo1nwWOJ6Su8lC1RbKbE6zskYUjyUxcBz5vDJvUgGuaAn3 BeA7Te5OQwv1Y0IZeNzmgLHONCCa8x2xDLtqQmlh~9CdpEzl n2DzLY1W1YDkQoeBWnO17Ys9yAw_&Key-Pair-Id= APKAJMGJRW6JX5OBM5LA, downloaded from the Internet May 18, 2016 (8 pages).

* cited by examiner

TECHNOLOGIES FOR CARTILAGE HARVESTING

CROSS-REFERENCE TO RELATED APPLICATIONS

This application claims a benefit of priority to U.S. Patent Application 62/325,615 filed on 21 Apr. 2016, which is herein fully incorporated by reference for all purposes.

TECHNICAL FIELD

Generally, the present disclosure relates to cartilage harvesting.

BACKGROUND

In the present disclosure, where a document, an act and/or an item of knowledge is referred to and/or discussed, then such reference and/or discussion is not an admission that the document, the act and/or the item of knowledge and/or any combination thereof was at the priority date, publicly available, known to the public, part of common general knowledge and/or otherwise constitutes prior art under the applicable statutory provisions; and/or is known to be relevant to an attempt to solve any problem with which the present disclosure is concerned with. Further, nothing is disclaimed.

A cartilage can be harvested via a blade and a mallet, such as via chiseling. However, such technique is imprecise, time-consuming, costly, and inefficient. Accordingly, there is a need to improve.

BRIEF SUMMARY

The present disclosure at least partially addresses at least one of the above. However, the present disclosure can prove useful to other technical areas. Therefore, the claims should not be construed as necessarily limited to addressing any of the above.

In an embodiment, a method comprises coupling a cutting head onto an actuator; applying a force to the cutting head via the actuator; and cutting a cartilage with the cutting head based on the force.

In an embodiment, a method comprises coupling an adapter to a rotary tool, wherein the adapter adapts the rotary tool from a rotary power to an impact power; coupling a cutting head to the adapter; applying a force to the cutting head via the adapter; and cutting a cartilage with the cutting head based on the force.

In an embodiment, a device comprises a cylinder including a sidewall and a base, wherein the sidewall includes an edge portion distal to the base, wherein the edge portion is configured for cutting; a tube extending from the base; and a plug hosted within the cylinder such that the base is positioned between the tube and the plug and such that the plug is able to travel within the cylinder along the sidewall.

In an embodiment, a device comprises an extracted chondrocyte including a sidewall and a top surface, wherein the sidewall is inclined from about five degrees to about twenty five degrees inclusively with respect to an axis perpendicular to the top surface.

The present disclosure may be embodied in the form illustrated in the accompanying drawings. However, attention is called to the fact that the drawings are illustrative. Variations are contemplated as being part of the disclosure, limited only by the scope of the claims.

BRIEF DESCRIPTION OF DRAWINGS

The accompanying drawings illustrate example embodiments of the present disclosure. Such drawings are not to be construed as necessarily limiting the disclosure. Like numbers and/or similar numbering scheme can refer to like and/or similar elements throughout.

DETAILED DESCRIPTION OF PREFERRED EMBODIMENTS

Figure 1:
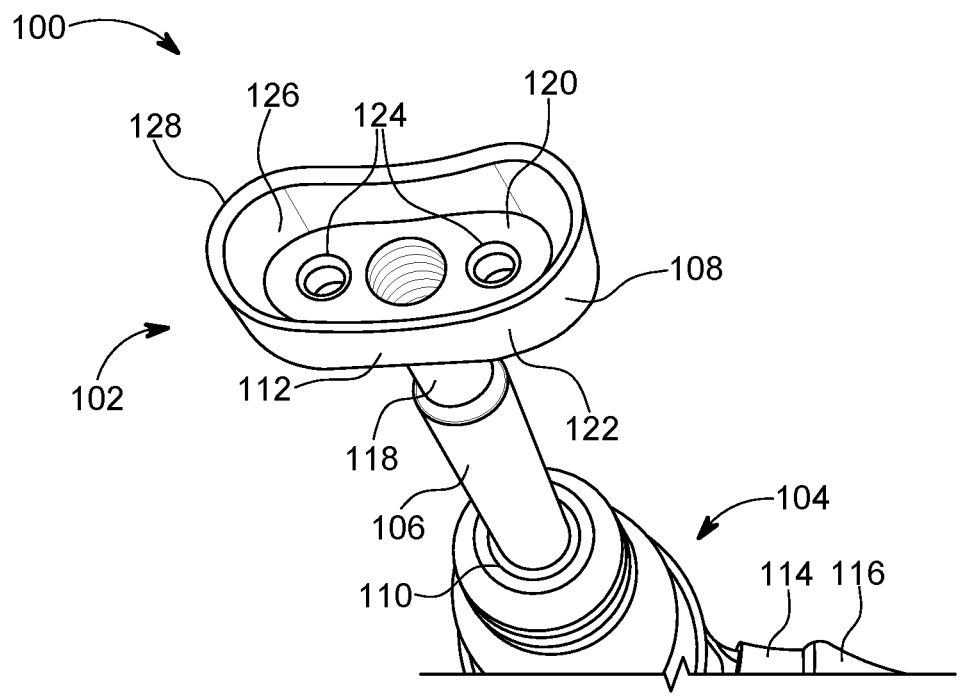
FIG. 1 shows an example embodiment of a device comprising a cutting tool and an actuator coupled to the cutting tool according to the present disclosure.

The present disclosure is now described more fully with reference to the accompanying drawings, in which example embodiments of the present disclosure are shown. The present disclosure may, however, be embodied in many different forms and should not be construed as necessarily being limited to the example embodiments disclosed herein. Rather, these example embodiments are provided so that the present disclosure is thorough and complete, and fully conveys the concepts of the present disclosure to those skilled in the relevant art.

Features described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity in any manner.

The terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

The terminology used herein is for describing particular example embodiments and is not intended to be necessarily limiting of the present disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence and/or addition of one or more other features, integers, steps, operations, elements, components, and/or groups thereof.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (30) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" can be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings were turned over, then the elements described as being on the "lower" side of other elements would then be oriented on "upper" sides of the other elements. Similarly, if the device in one of the figures were turned over, elements described as "below" or "beneath" other elements would then be oriented "above" the other elements. Therefore, the example terms "below" and "lower" can encompass both an orientation of above and below.

As used herein, the term "about" and/or "substantially" refers to a +/−10% variation from the nominal value/term. Such variation is always included in any given value/term provided herein, whether or not such variation is specifically referred thereto.

If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

FIG. 1 shows an example embodiment of a device comprising a cutting tool and an actuator coupled to the cutting tool according to the present disclosure. In particular, a device 100 includes a cutting tool 102 and an actuator 104. The cutting tool 102 is T-shaped as defined via a bar 106 and a platform 108. The cutting tool 102 is an assembly, but can be unitary.

The bar 106, whether solid or hollow, comprises a first end portion 110 and a second end portion 112, as visible external to the actuator 104. Note that the bar 106 may have a portion that extends into the actuator 104 such that the portion is not externally visible, with the first end portion 110 being positioned between the second end portion 112 and the portion that is not externally visible. The bar 106 is coupled to the actuator 104 via the first end portion 110, such as via being threaded/fastened, but other ways of coupling can be used, such as mating. The bar 106 is coupled to the platform 108 via the second end portion 112, such as via being threaded/fastened, but other ways of coupling can be used, such as mating.

The platform 108 includes a tube 118, a plate 120, and a skirt/wall 122. The tube 118 extends from the plate 120 in a T-shape manner. The skirt/wall 122 depends from the plate 120 such that a volume of space 126 is enclosed by the plate 120 and the skirt/wall 122. The plate 120 defines a plurality of apertures 124 therethrough such that the tube 118 is positioned between the apertures 124 and the volume of space 126 is accessible through the apertures 124, such as visually or fluidly. The apertures 124 can be identical to or different from each other in size, depth, or shape. The skirt/wall 122 is solid, but can be perforated. The tube 118 is internally threaded. The tube 118 orthogonally extends from the plate 120, but non-orthogonal extension is possible. Note that the tube 118 can be coupled to the plate 120, such as adhesively, fastenably, or mated, although unitary configuration is possible. The tube 118 couples to the second end portion 112 of the bar 106 via threading, although other coupling techniques are possible, such as adhering, magnetizing, fastening, mating, interlocking, brazing, or others. The skirt/wall 122 perimetrically extends in a closed shape, such as an O-shape, a D-shape, an 8-shape, or others, but an open shape is possible, such as a U-shape, a C-shape, or others. Such extension can be rectilinear, wavy, arcuate, pulsating, or other extensions. The skirt/wall 122 can be tapered away or towards the tube 118.

The skirt/wall 122 includes a lowermost edge portion 128 distal to the plate 120. The lowermost edge portion 128 can be serrated or sharp or comprise a blade portion. For example, the lowermost edge portion 128 can be arcuate, whether longitudinally or laterally to the skirt/wall 122. For example, the lowermost edge portion 128 can be beveled such as from about 5 degrees to about 25 degrees. In some embodiments, the skirt/wall 122 can be nested, inwardly or outwardly, such that a lower portion thereof, with the lowermost edge portion 128, telescopes toward or away from the tube 118.

The actuator 106 includes a pistol grip 114 with a trigger 116 to activate an actuation, whether rotary or linear. Note though that other types of actuators can be used, such as tubular or without the pistol grip 114. The actuator 106 can be pneumatic, electric/battery, hydraulic, thermal, mechanical, or other types. The actuator 106 periodically provides an impact force to the platform 108 via the bar 106 from the first end portion 110 to the second end portion 112. The impact force can be periodic, such as from about two impacts per second to about five hundred impacts per second, although other impact configurations are possible, such as less than two impacts per second or greater than five hundred impacts per second.

Figure 2:
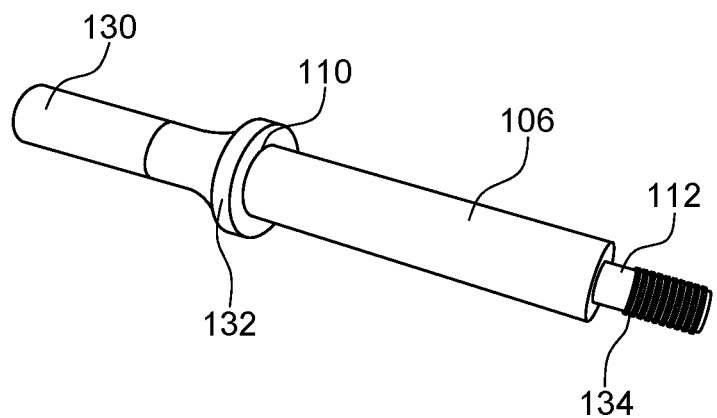
FIGS. 2-9 show an example embodiment of a cutting tool disassembled according to the present disclosure.
Figure 3:
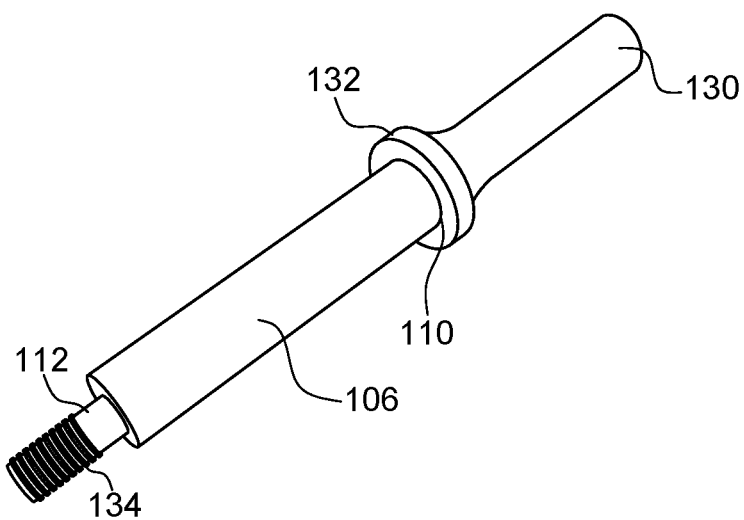
Figure 4:
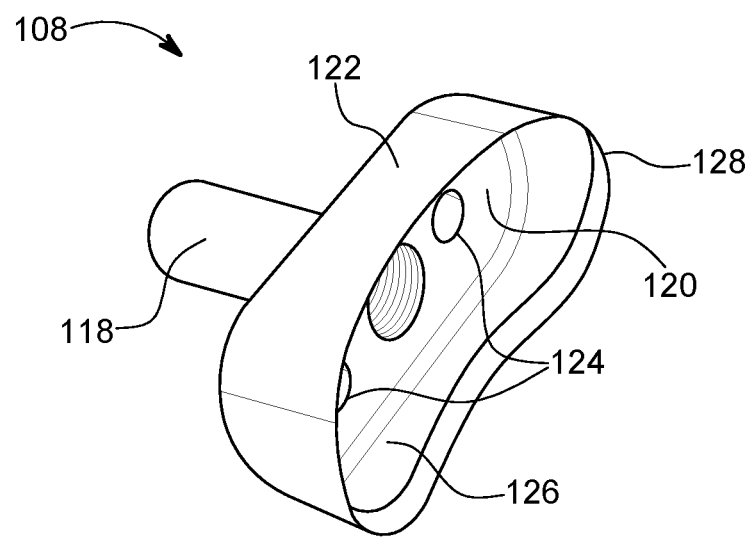
Figure 5:
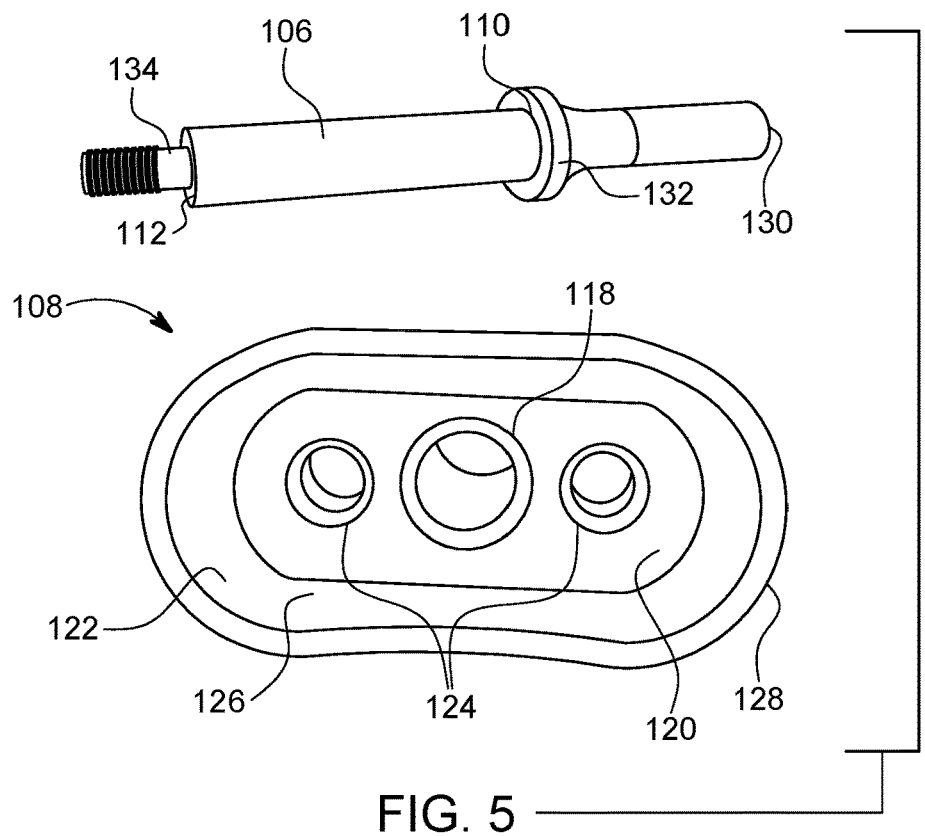
Figure 6:
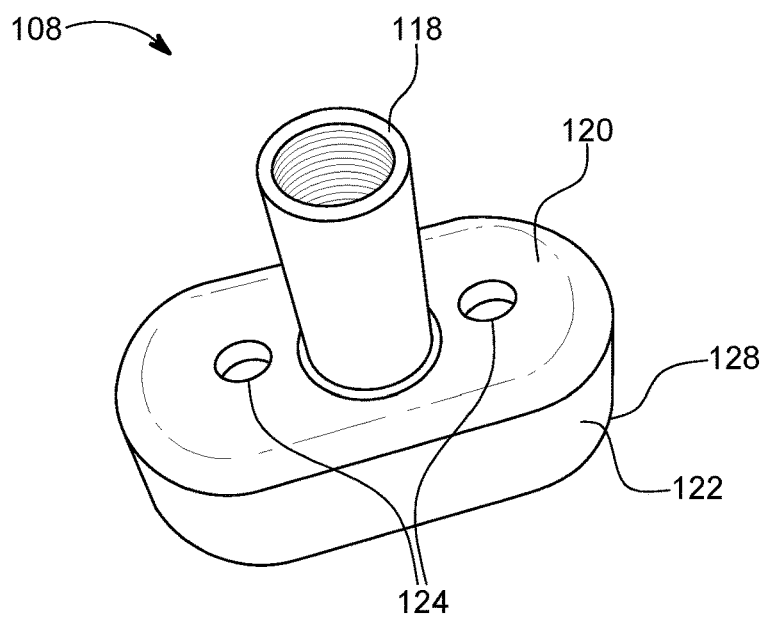
Figure 7:
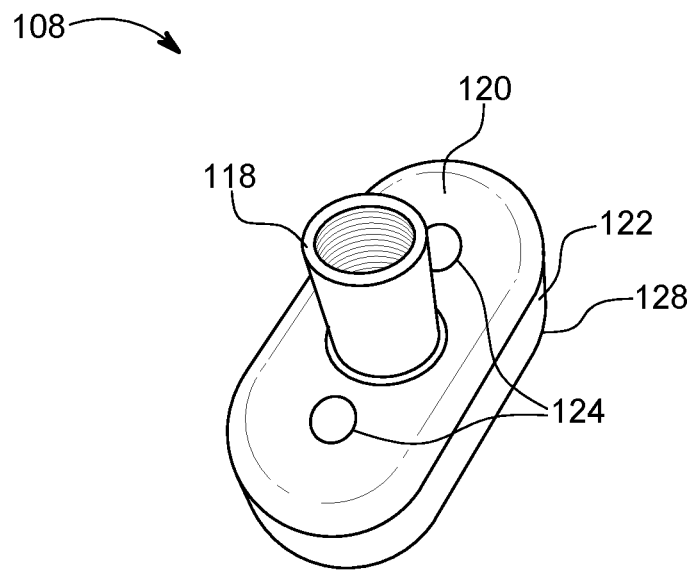
Figure 8:
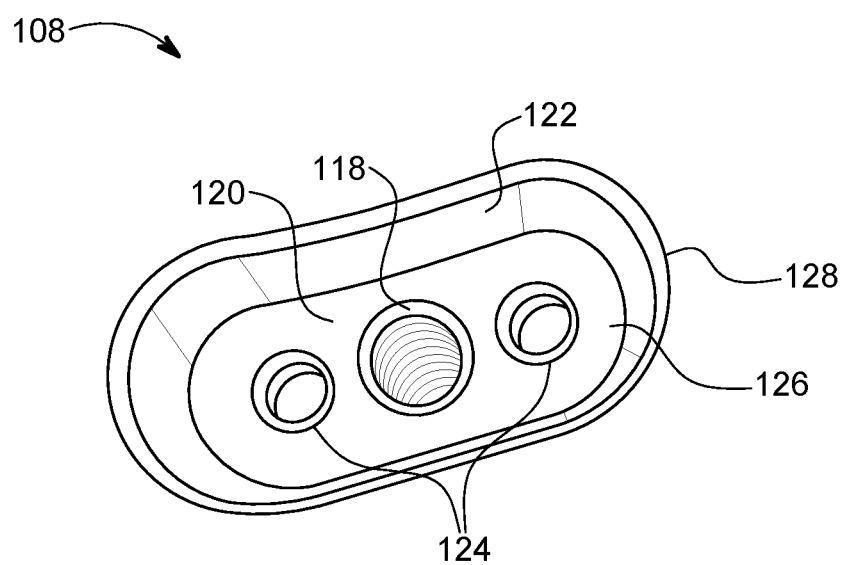
Figure 9:
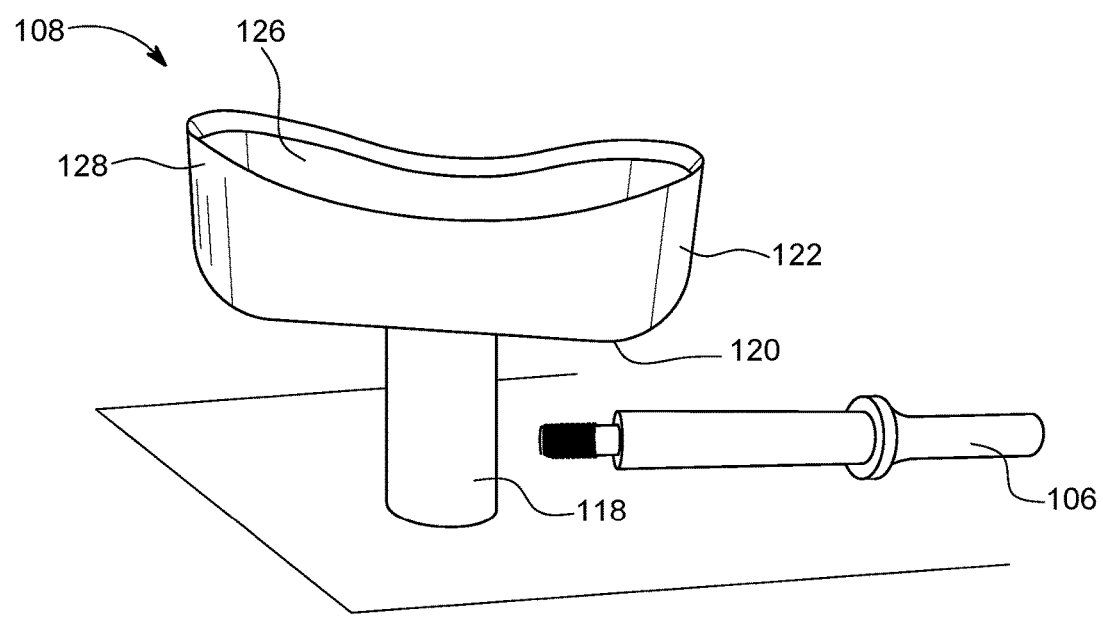

FIGS. 2-9 show an example embodiment of a cutting tool disassembled according to the present disclosure. In particular, as shown in FIGS. 2-3, the first end portion 110 is structured to engage the actuator 104, such as via securely mating, although other engaging techniques are possible, such as fastening, adhering, magnetizing, brazing, or others. The bar 106 includes a portion 130 that extends into the actuator 104 such that the portion 130 is not externally visible, with the first end portion 110 being positioned between the second end portion 112 and the portion 130 that is not externally visible. The second end portion 112 of the bar 106 includes a shaft 134 that is threaded, such as for coupling to the tube 118. The bar 106 hosts a disc 132, whether unitary or assembled thereto, between the second end portion 112 and the portion 130 to contact or rest against the actuator 104. The bar 106 is solid, but can be hollow. The bar 106 is metallic, but can include plastic, wood, rubber, or other materials.

As shown in FIGS. 4-9, the platform 108 includes the tube 118, the plate 120, and the skirt/wall 122. The tube 118 extends from the plate 120 in a T-shape manner. The skirt/wall 122 depends from the plate 120 such that the volume of space 126 is enclosed by the plate 120 and the skirt/wall 122. The plate 120 defines the apertures 124 therethrough such that the tube 118 is positioned between the apertures 124 and the volume of space 126 is accessible through the apertures 124, such as visually or fluidly. The apertures 124 can be identical to or different from each other in size, depth, or shape. The skirt/wall 122 is solid, but can be perforated. The tube 118 is internally threaded. The tube 118 orthogonally extends from the plate 120, but non-orthogonal extension is possible. Note that the tube 118 can be coupled to the plate 120, such as adhesively, fastenably, or mated, although unitary configuration is possible. The tube 118 couples to the second end portion 112 of the bar 106 via threading, although other coupling techniques are possible, such as adhering, magnetizing, fastening, mating, interlocking, brazing, or others. The skirt/wall 122 perimetrically extends in a closed shape, such as an O-shape, a D-shape, an 8-shape, or others, but an open shape is possible, such as a U-shape, a C-shape, or others. Such extension can be rectilinear, wavy, arcuate, pulsating, or other extensions. The skirt/wall 122 includes the lowermost edge portion 128 distal to the plate 120. The lowermost edge portion 128 can be serrated or sharp or comprise a blade portion. For example, the lowermost edge portion 128 can be arcuate, whether longitudinally or laterally to the skirt/wall 122.

In some embodiments, the skirt/wall 122 can include a sensor to sense an ambient property during harvesting, such as temperature, pressure, movement, angling, orientation, path, or other relevant ambient properties. The sensor can output data to a computing device, such as over a local wireless communication. The sensor can be powered via the actuator 104, such as through wiring within or on the bar 106, or wirelessly, such as via radio or induction. Note that more than one of such sensors is possible.

Figure 10:
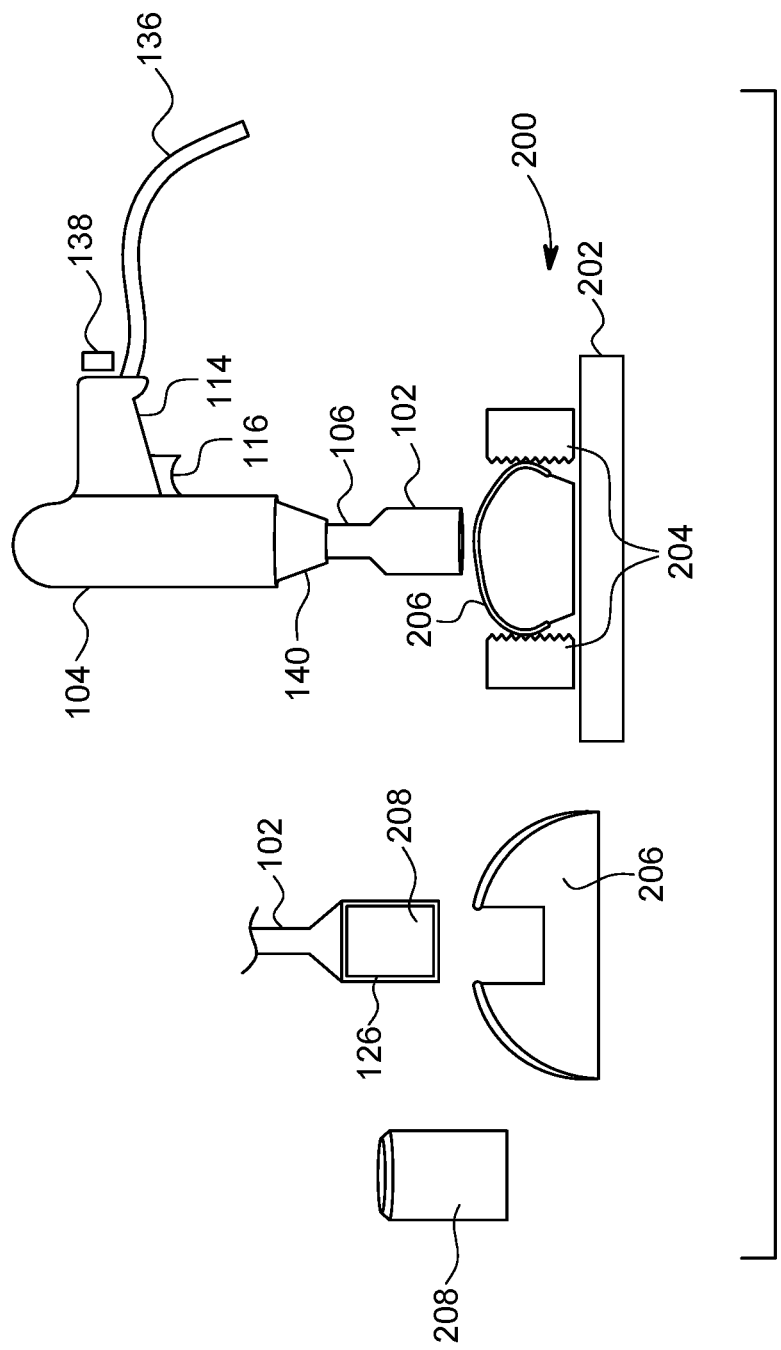
FIG. 10 shows an example embodiment of a method for harvesting a cartilage according to the present disclosure.

FIG. 10 shows an example embodiment of a method for harvesting a cartilage according to the present disclosure. As shown, a method 200 can be used to harvest an osteochondral allograft 208 using a pneumatic actuator, such as the actuator 104, to powerably drive a cutting head, such as the cutting tool 102. For example, the method 200 can comprise coring a cartilage tissue 206. In particular, by using the pneumatic actuator, such as the actuator 104 that is fluidly powered via a hose 136, a user can attach a cutting head, such as the cutting tool 102, of various shapes and depths to a barrel tip 140 of the pneumatic actuator, such as the actuator 104, and line the cutting head, such as the cutting tool 102, up on a graft, such as the cartilage tissue 206, in a vise 204 and resting on a platform 202, where the user desires to cut a smaller graft, such as the osteochondral allograft 208, for implanting onto a patient or other uses, such as medical research. Note that the platform 202 and the vise 204 form a graft holding stage. Once a location, such as a defined area, on a door graft, such as the cartilage tissue 206, is determined via the user, such as via writing/drawing on the door graft, the user uses a regulator 138 of the pneumatic actuator, such as the actuator 104, to adjust an actuating force. Then, the user slowly increases the actuating force to bring up an impact power to a point at which the user can cut through a cartilage layer of the cartilage tissue 206 and deep into a subchondral bone, such as a femur. This technique can be done in lieu of manual power via a mallet and a cutting head mounted to an impactable handle, such as a chisel. Once the user has reached a desired depth, the user releases the smaller graft, such as the osteochondral allograft 208, by use of a saw (whether a hand saw or a mechanically powered saw—circular, reciprocating, continuous band, chainsaw), a blade, a knife, a machete, or other cutting tool to cut on a perpendicular plane of a newly cut graft, such as the osteochondral allograft 208. For example, the perpendicular plane is perpendicular to the bar 106 or the tube 118. Subsequently, the user may withdraw the cutting tool or the pneumatic actuator, such as the actuator 104, and release the newly cut graft for implant into the patient or other uses, such as medical research. For example, the newly cut graft, such as the osteochondral allograft 208, can be positioned within the volume of space 126 enclosed by the plate 120 and the skirt/wall 122.

Note that such technique is an example and other structures or devices can be used, such as a non-pneumatic actuator. Further, note that any cartilage, whether elastic cartilage, hyaline cartilage, or fibrocartilage, or bone tissue can be used. For example, such tissue can be in or near joins, between bones, rib cage, ear, nose, bronchial tubes, trachea rings, or intervertebral discs.

In some embodiments, the osteochondral allograft 208 can be pushed out of the platform 108, in a manual or powered manner, via a plunger inserted, in a manual or powered manner, through one or all of the apertures 124 or the tube 118. The plunger can be T-shaped or H-shaped. The plunger can be telescoped through, in a manual or powered manner, and expanded, in a manual or powered manner, within the volume of space 126.

In some embodiments, the osteochondral allograft 208 can be pushed out of the platform 108, in a manual or powered manner, via the plate 120 moving along the skirt/wall 122 away from the tube 118, in a manual or powered manner. The movement can be via gears, tracks, ratchets, or wheels hosted via the skirt/wall 122.

In some embodiments, the osteochondral allograft 208 can be removed from the platform 108, in a manual or powered manner, via the skirt/wall 122 telescopingly contracting/raising toward the plate 120, in a manual or powered manner, or hingedly pivoting/raising with respect to the plate 120 toward the plate 120, which may include co-planar with the plate 120 or lower or higher. Note that the skirt/wall 122 can include a plurality of skirt/walls 122, whether in contact with each other or avoiding contact with each other, arranged or extending as disclosed herein, with gaps between the skirt/walls 122 being possible, although a gapless configuration is possible as well. Further, note that the skirt/walls 122 can interlock, such as via mating, fastening, adhering, or others.

Figure 11:
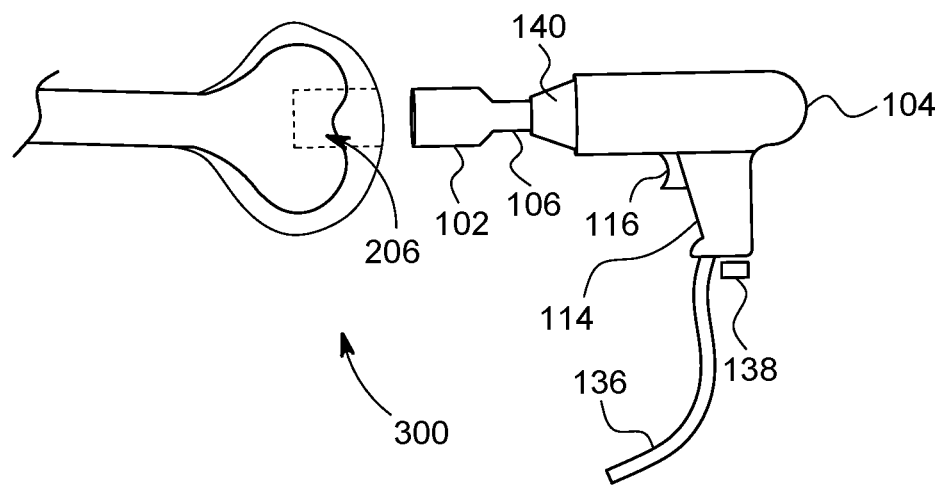
FIG. 11 shows an example embodiment of a method for defect removal according to the present disclosure.

FIG. 11 shows an example embodiment of a method for defect removal according to the present disclosure. A method 300 is similar to the method 200. Such defect can comprise any tissue, such as bone or cartilage, desired to be extracted, as disclosed herein.

Figure 12:
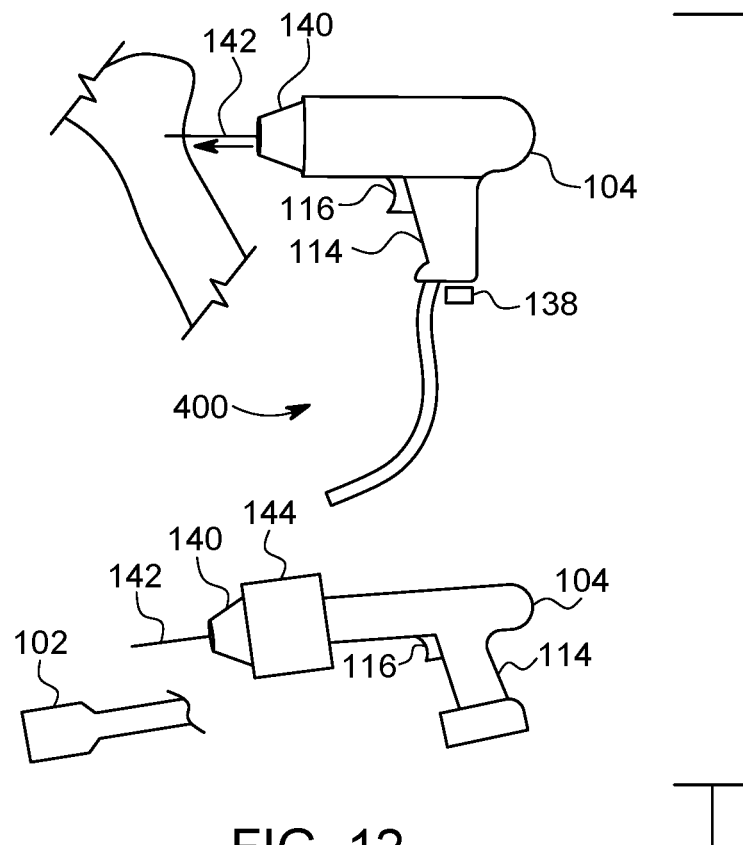
FIG. 12 shows an example embodiment of a method for driving a pin into a bone according to the present disclosure.

FIG. 12 shows an example embodiment of a method for driving a pin into a bone according to the present disclosure. A method 400 is similar to the method 200 or the method 300. A pin 142 can be securely positioned within a tube coupled, such via the barrel tip 140, to the actuator, such as the actuator 104, and the actuator, such as the actuator 104, can provide the impact force to drive the pin 142. Note that the pin 142 can be unitary or assembled, such as via adhering, fastening, mating, interlocking, brazing, or others, and can include metal, plastic, wood, rubber, or other materials.

In some embodiments, an adapter 144 can be structured to couple a rotary tool, such as a drill, a powered screwdriver, or others, and a cutter, such as the cutting tool 102, or the pin 142, such as disclosed herein. The adapter 144 converts a rotary power to an impact power, such as for use in a drill, a powered screwdriver, or others. Some examples of such adapter can comprise technologies disclosed in U.S. Pat. Nos. 6,264,211 and 8,622,667 and US Patent Application Publication 2007/0131440, all of which are fully incorporated by reference herein for all purposes. As such, with the adapter 144, the rotary tool can operate as the actuator 104.

Figure 13:
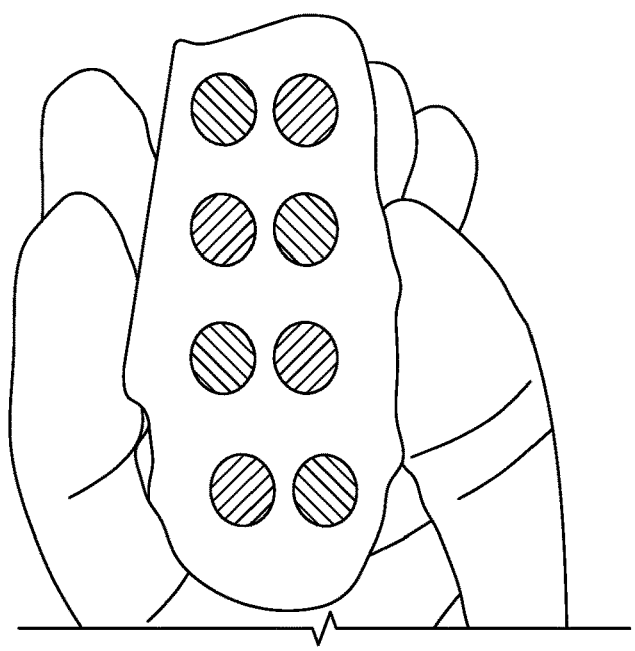
FIG. 13 shows a region of a hemicondyle according to the present disclosure.

In some embodiments, various techniques disclosed herein may result in higher chondrocyte viability at a periphery of a graft, such as the osteochondral allograft 208. In particular, harvesting of donor osteochondral grafts may subject an articular cartilage to a mechanical damage and subsequent apoptotic cell death. Manual harvest with a use of cylindrical osteotomes may result in an extensive zone of chondrocyte death extending approximately 0.4 mm from an edge of the graft. Powered coring devices are likely to cause even greater cell death than manual punches, despite continuous irrigation to limit thermal necrosis. Some studies have found significantly decreased chondrocyte viability in dowels (2.7 and 4.5 mm diameter) harvested from a femoral trochlea of a sheep using a powered coring reamer compared to manual punches. Furthermore, harvesting of large donor grafts ($\geq 15$ mm), which currently is performed exclusively using powered coring devices, likely induces more thermal necrosis than harvesting of smaller donor grafts due to a larger circumference needed to cut. Currently, there are no alternative harvesting techniques to a powered coring reamer when harvesting osteochondral grafts $\geq 1.5$ mm. Ultimately, viable chondrocytes in osteochondral allografts at the time of transplantation are likely responsible for maintenance of long-term survival and function of the donor articular cartilage. As such, various techniques disclosed herein enable harvesting of osteochondral grafts using a pneumatic punch and may result in higher chondrocyte viability at the periphery of the graft compared to the powered coring reamer. For example, to confirm that various techniques disclosed herein provide various benefits of pneumatic punch over powered coring reamer harvesting techniques on chondrocyte viability, one may employ dowels 15 mm in diameter that may be harvested from fresh human femoral hemicondyle allografts (30 mm diameter can be used as well) to a depth of 10 mm. As shown in FIG. 13, dowels may be harvested in pairs (one using each technique) from a same region of the hemicondyle to allow for pairwise comparisons. In FIG. 13, blue icons correspond to pneumatic punch and red icons correspond to powered coring reamer. Continuous saline irrigation may be applied during both harvesting techniques. Pairs may then be placed in 10% PFA immediately after harvest or placed in nutrient media for 3 days at 37° C. prior to 10% PFA fixation.

Note that an endpoint analysis includes (1) Cell Viability—TUNEL staining and (2) Safranin-O Staining—a modified Mankin scale may be used to evaluate structure, cellularity, and safranin-O staining as a marker for PG (growth factor) content. Also, note that a visual analysis includes a visual analysis of edges of allografts. Further, note that a statistical analysis includes pairwise comparisons that may be made for each pair of dowels harvested. Comparisons of outcomes between day 0 and day 3 may also be performed—checking for continued necrosis over time and additional staining.

Figure 14:
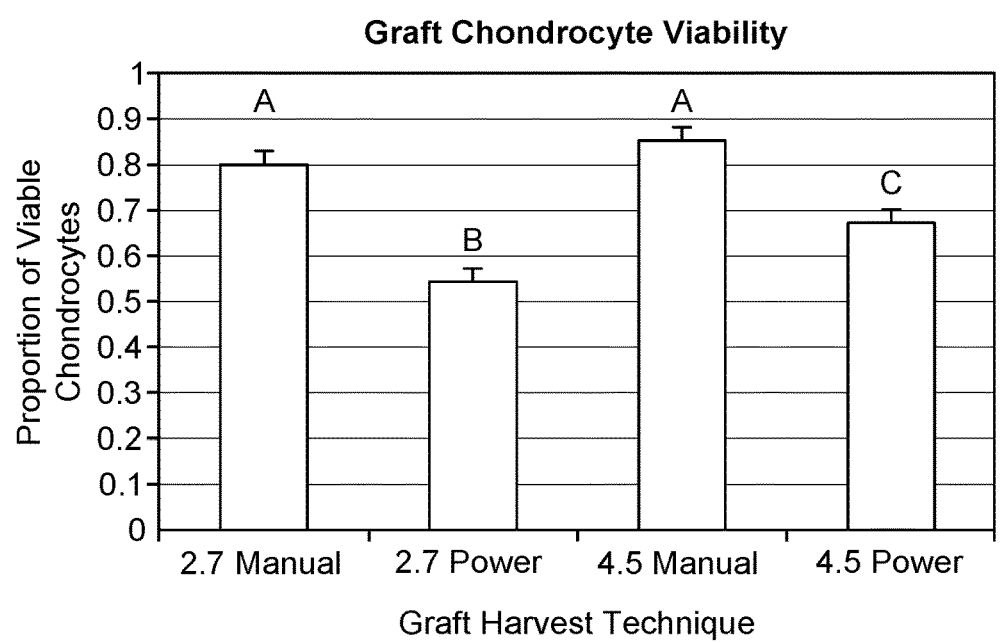
FIG. 14 shows a bar diagram informative of a graft chondrocyte viability according to the present disclosure.

FIG. 14 shows a bar diagram informative of a graft chondrocyte viability according to the present disclosure. As shown, the bar diagram is based on a cell viability graft derived from completed research. The manual columns represent a cutter that is driven with a mallet. The power columns represent a cutter that is actuated using a rotary cutting tool. The present disclosure discloses technology that will result in similar viability proportions as the manual method, while providing a faster and more suitable method for chondrocyte preparation.

Figure 15:
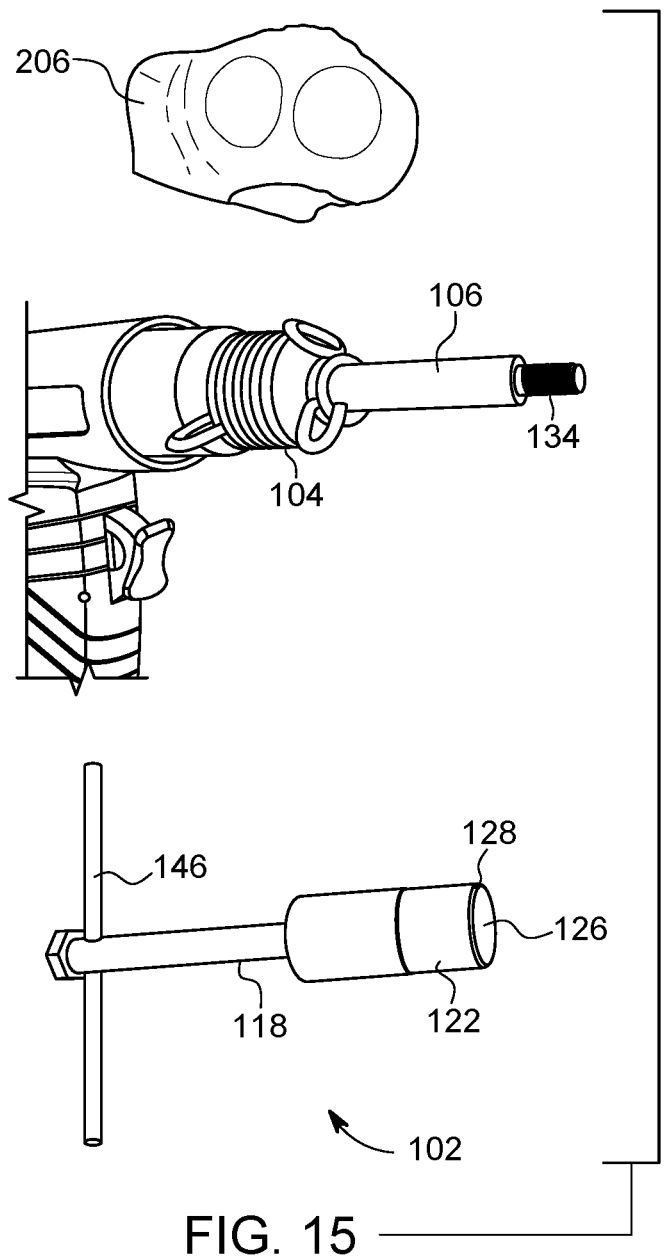
FIGS. 15-30 show various example embodiments of a cutting tool according to the present disclosure.

FIGS. 15-30 show various example embodiments of a cutting tool according to the present disclosure. In particular, FIG. 15 shows that the cutting tool 102 includes a solid or hollow shaft 146 that removably or non-removably extends through the tube 118 such that the shaft 146 and the tube 118 form a T-shape thereby, although an L-shape is possible as well. Such configuration can enable a provision of a force, whether manual or powered, whether rotary (fastening), rectilinear (pressure toward the lowermost edge portion 128), or others. The shaft 146, whether unitary or assembled, can include metal, plastic, wood, rubber, or other materials. The shaft 146 is rectilinear, but can extend in other configurations, such as arcuate, sinusoidal, or others.

Figure 16:
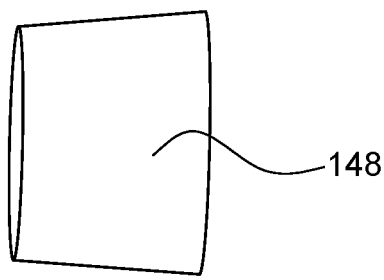

As shown in FIG. 16, the cutting tool 102 may host an extruder plug 148 within the volume of space 126. The plug 148 may be formed from delrin. The plug 148 may include a lower surface that defines an inward or outward dimple 150 therein or the lower surface can be radially or diametrically rectilinear or arcuate as viewed from side view. Note that the plug 148 can include other materials, whether additional or alternative to delrin, such as metal, rubber, wood, plastic, or others. The plug 148 includes a $2/1000$th" taper toward an outside of the skirt/wall 122 along a cutting working length thereof, such as along the skirt/wall 122, which may include the lowermost edge portion 128. Given a larger diameter of such harvesting device, which one can accurately drive via pneumatic actuation, one can have a larger cumulative area of surface contact along a wall(s) of the cutting tool 102 juxtaposing a graft bone. Such taper helps to relieve a friction for withdrawal of the cutting tool 102. Note that such tapering is illustrative and other suitable variations, whether larger or smaller are possible, such as $1/1000$th", $3/1000$th", or others. For example, such tapering can be from about $1/1000$" to about $1/100$" to act as an impact brake or shock absorber. In some embodiments, the cutting tool 102 may host a rigid plate within the volume of space 126. The rigid plate may be positioned between the plate 120 and the plug 148. The rigid plate may engagedly contact the plug 148 such that when a pressure in a direction away from the plate 120 toward the lowermost edge portion 128 is applied onto the rigid plate, then the rigid plate engages the plug 148 to move the plug 148 within the volume of space 126 such that the plug 148 travels along the sidewall 122. Such configuration may be useful if the plug 148 includes a non-rigid or flexible substance, such as rubber.

In some embodiments, there is a slight reverse taper added to the plug 148 to limit a surface impact pressure on a cartilage surface upon impaction for harvest. This too may be a $2/1000$th" taper, although other suitable variations are possible, whether larger or smaller, such as $1/1000$th", $3/1000$th", or others. The plug 148 will slowly with gradual pressure increase, wedge itself against an inner walls of the cutting tool 102, such as along the skirt/wall 122, which may include the lowermost edge portion 128. Further, a radius may be added to the graft contact side of the plug 148 to more closely match a radius of curvature of the femoral condyle thereby seeking to reduce point loading on the chondral surface of the harvested graft. Such techniques may provide at least a 30-40% reduction in thermal (Cellular) necrosis using pneumatic harvest over rotary devices. Such techniques may also provide a 30% reduction in edge profile roughness.

Figure 17:
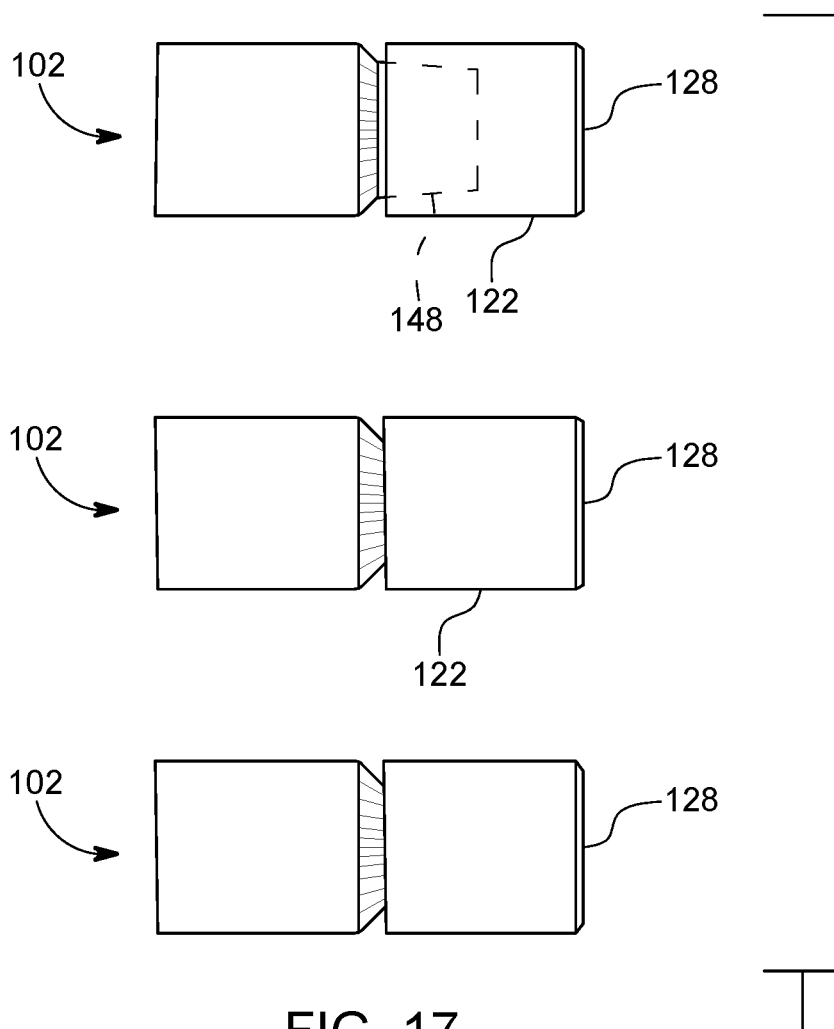
Figure 18:
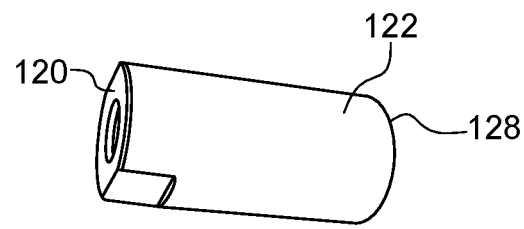
Figure 19:
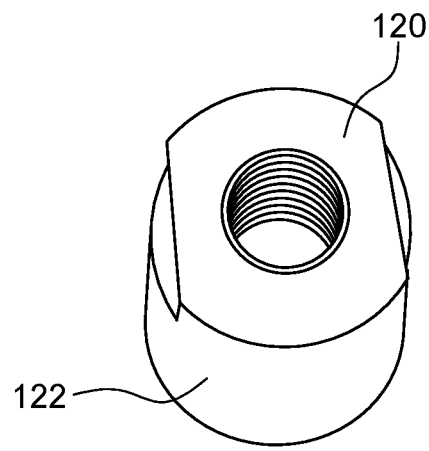
Figure 20:
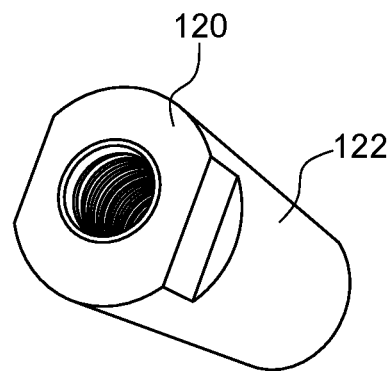
Figure 21:
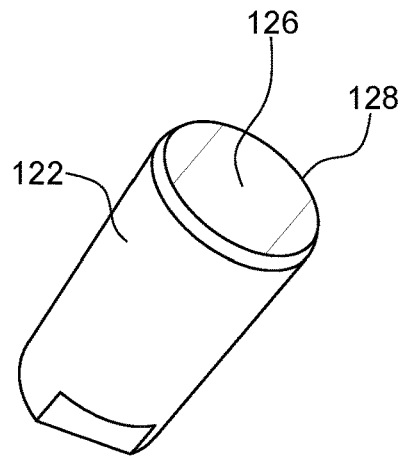
Figure 22:
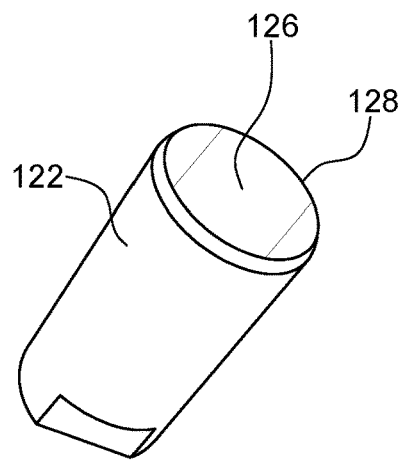
Figure 23:
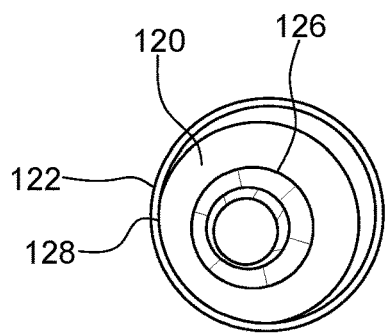
Figure 24:
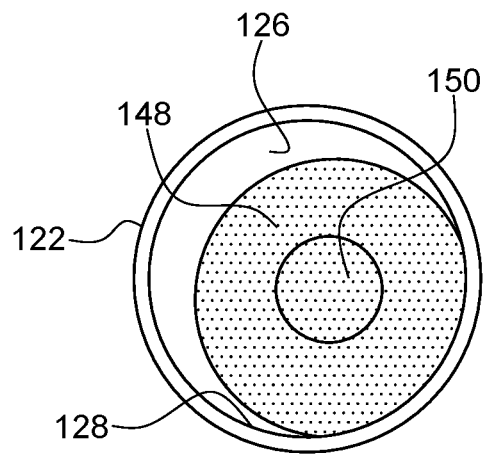
Figure 25:
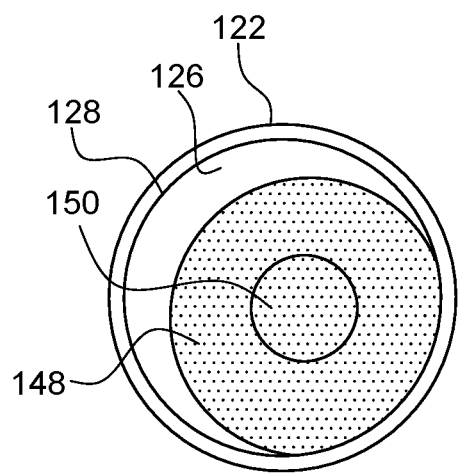
Figure 26:
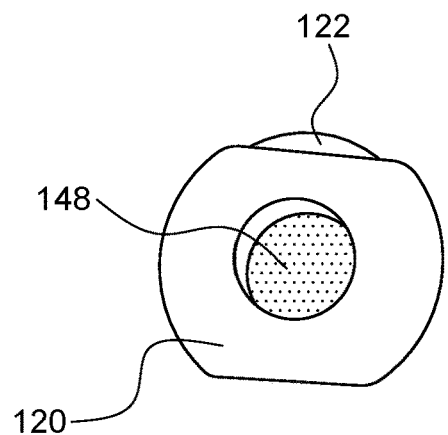
Figure 27:
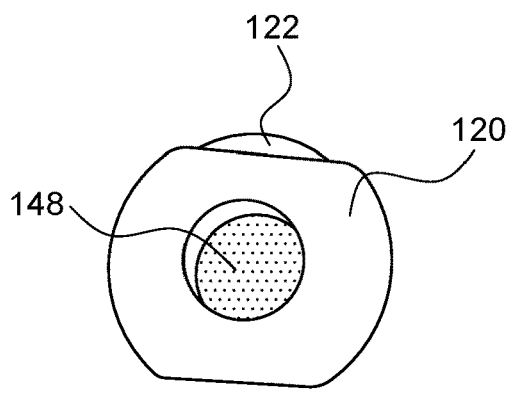
Figure 28:
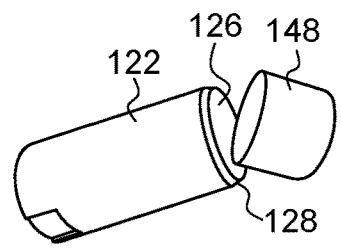
Figure 29:
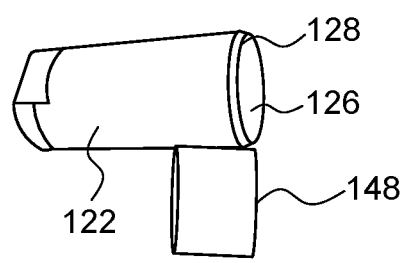
Figure 30:
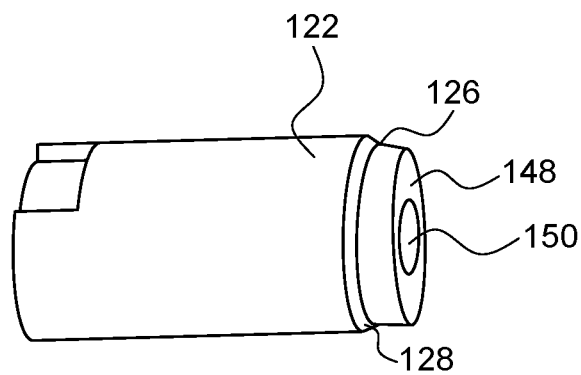

As shown in FIG. 17, the cutting tool 102 may include a $2/1000$" taper on an outside or inside of the skirt/wall 122, such as the skirt/wall 122 being sider on top than bottom or vice versa, although other tapering, as disclosed herein, is possible. The lowermost edge portion may be beveled from about 5 degrees to about 25 degrees.

The skirt/wall 122 extends about the plug 148 that may include the dimple or be arcuate, with the plug 148 being tapered to be wider at bottom or vice versa. The plug 148 may be tapered as disclosed herein, such as $2/1000$" or others as disclosed herein. In some embodiments, the skirt/wall 122 may have a longitudinal external height of about 15 millimeters and an inner diameter of about 16 millimeters, although any suitable variations are possible for any dimension, such as from about 1 millimeter to about 100,000 millimeters or more. The lowermost edge portion 128 may be beveled and have an inside taper be from about $1/1000$" to about $1/100$" or others to be wider at bottom of the skirt/wall 122 or vice versa.

FIGS. 18-30 shows various views of the skirt/wall 122 extending about the volume of space 126 which may contain the plug 148 that can travel along the skirt/wall 122 away from the plate 120 toward the lowermost edge portion 128.

In some embodiments, using various techniques disclosed herein, a device can comprise an extracted chondrocyte, such as the osteochondral allograft 208, including a sidewall and a top surface, where the sidewall is inclined from about five degrees to about twenty five degrees inclusively with respect to an axis perpendicular to the top surface. Note that this includes five, six, seven, eight, nine, ten, eleven, twelve, thirteen, fourteen, fifteen, sixteen, seventeen, eighteen, nineteen, twenty, twenty one, twenty two, twenty three, twenty four, twenty five, and any values therebetween in any combinatory manner. Note that a cutting tool, such as the cutting tool 102, can host the extracted chondrocyte. The sidewall may be planar and smooth or rough. The extracted chondrocyte may have less necrosis than a chondrocyte extracted using a rotary device. The extracted chondrocyte may have less edge profile roughness than a chondrocyte extracted using a rotary device. The edge profile roughness may be inclusively from about 0.1% to about 30%, which may be surface area or roughness degree, including any values therebetween in any combinatory manner, similarly to as noted above. For example, the edge profile roughness may be measured using a Roughness Average (Ra) or Root Mean Square (RMS), with the RA being calculated as a roughness average of a surface's measured microscopic peaks and valleys and the RMS being calculated as a root mean square of a surface's measured microscopic peaks and valleys. The extracted chondrocyte may have less dead cells than a chondrocyte extracted using a rotary device.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The corresponding structures, materials, acts, and equivalents of all means or step plus function elements in the claims below are intended to include any structure, material, or act for performing the function in combination with other claimed elements as specifically claimed. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The description of the present disclosure has been presented for purposes of illustration and description, but is not intended to be fully exhaustive and/or limited to the disclosure in the form disclosed. Many modifications and variations in techniques and structures will be apparent to those of ordinary skill in the art without departing from the scope and spirit of the disclosure as set forth in the claims that follow. Accordingly, such modifications and variations are contemplated as being a part of the present disclosure. The scope of the present disclosure is defined by the claims, which includes known equivalents and unforeseeable equivalents at the time of filing of the present disclosure.

What is claimed is:

1. A method comprising:
    coupling a cutting head onto an actuator, wherein the cutting head is coupled to the actuator via a shaft, wherein the shaft includes a first end portion, a second end portion, and a disc portion, wherein the disc portion is positioned between the first end portion and the second end portion, wherein the first end portion is coupled to the actuator such that the first portion is not visible external to the actuator, wherein the disc portion engages the actuator such that the disc portion is visible external to the actuator, wherein the second end portion is fastened to the cutting head;
    applying a force to the cutting head via the actuator; and
    cutting a cartilage with the cutting head based on the force.

2. The method of claim 1, wherein the cutting head includes a plate, a tube, and a skirt, wherein the plate and the tube form a T-shape, wherein the skirt depends from the plate in a direction away from the tube such that the plate and the skirt define an open space, wherein the cutting includes positioning the cartilage within the open space.

3. The method of claim 2, wherein the tube is coupled to the actuator.

4. The method of claim 3, wherein the tube is coupled to the actuator via fastening.

5. The method of claim 2, wherein the plate defines a plurality of apertures such that the tube extends from the plate between the apertures.

6. The method of claim 2, wherein the skirt includes an edge portion distal to the plate, wherein the edge portion is at least one of serrated, sharp, rectilinear, arcuate, not rectangular, or extends in a closed shape.

7. The method of claim 1, wherein the actuator is at least one of pneumatic or rotary.

8. The method of claim 1, wherein the actuator hosts an adapter that converts a rotary power to an impact power, wherein the force is based on the impact power.

9. The method of claim 1, wherein the cutting head includes a metal.

10. The method of claim 1, wherein the force is from about two impacts per second to about five hundred impacts per second.

11. The method of claim 1, wherein the cartilage is hosted via a subchondral bone.

12. The method of claim 1, further comprising:
    releasing the cartilage from the cutting head.

13. The method of claim 12, wherein the releasing includes cutting the cartilage external to the cutting head while the cartilage is hosted via the cutting head.

14. The method of claim 1, wherein the cartilage includes at least one of an osteochondral allograft or a bone tissue.

15. The method of claim 1, wherein the cartilage includes at least one of an elastic cartilage, a hyaline cartilage, or a fibrocartilage.

16. The method of claim 1, wherein the cartilage is hosted in at least one of a rib cage, an ear, a nose, a bronchial tube, a trachea ring, or an intervertebral disc.

17. The method of claim 1, further comprising:
    pushing the cartilage out from the cutting head.

18. The method of claim 17, wherein the pushing is via at least one of a plunger inserted into the cutting head, a plate of the cutting head moving away from the actuator, or a plug hosted within the cutting head.

19. The method of claim 1, wherein the cutting head is cylindrical.

* * * * *